United States Patent
Iwama

(10) Patent No.: US 7,431,985 B2
(45) Date of Patent: Oct. 7, 2008

(54) MEDICAL PRESSURE-SENSITIVE ADHESIVE COMPOSITION, PROCESS FOR PRODUCING THE SAME, AND MEDICAL TAPE

(75) Inventor: Akio Iwama, Otsu (JP)

(73) Assignees: Lintec Corporation, Tokyo (JP); PIAC Co., Ltd., Shiga (JP)

( * ) Notice: Subject to any disclaimer, the term of this patent is extended or adjusted under 35 U.S.C. 154(b) by 260 days.

(21) Appl. No.: 11/512,700

(22) Filed: Aug. 30, 2006

(65) Prior Publication Data

US 2006/0292365 A1 Dec. 28, 2006

Related U.S. Application Data

(63) Continuation of application No. 10/504,180, filed as application No. PCT/JP02/13695 on Dec. 26, 2002, now abandoned.

(30) Foreign Application Priority Data

Feb. 14, 2002 (JP) .............................. 2002-036152

(51) Int. Cl.
*B32B 7/12* (2006.01)

(52) U.S. Cl. ................................ 428/355 AC; 526/931

(58) Field of Classification Search ................ 526/931; 525/221; 428/355 R, 355 EN, 355 AC
See application file for complete search history.

(56) References Cited

U.S. PATENT DOCUMENTS

| 4,364,972 A | 12/1982 | Moon |
| 4,370,380 A | 1/1983 | Shah |
| 5,312,868 A | 5/1994 | Abe et al. |
| 5,648,166 A | 7/1997 | Dunshee |
| 5,902,678 A | 5/1999 | Konda et al. |

FOREIGN PATENT DOCUMENTS

| EP | 0819713 A1 | 1/1998 |
| JP | 56-008476 | 1/1981 |
| JP | 59-199628 | 11/1984 |
| JP | 62-077316 | 4/1987 |
| JP | 63-305873 | 12/1988 |
| JP | 05-065460 | 3/1993 |
| JP | 05-139960 | 6/1993 |
| JP | 06-004533 B | 1/1994 |
| JP | 2000-044904 | 2/2000 |

*Primary Examiner*—Thao T. Tran
(74) *Attorney, Agent, or Firm*—Carmody & Torrance LLP

(57) ABSTRACT

A medical pressure-sensitive adhesive composition having excellent re-adhesion property, and also excellence in both the peel adhesion property and the low skin stimulus property, a process for producing the same, and a medical tape are provided. In the medical tape, a medical pressure-sensitive adhesive composition containing acrylic polymer and acrylic oligomer is laminated on a substrate, wherein the medical pressure-sensitive adhesive composition is prepared by cross-linking an intermediate composition containing an acrylic polymer having a cross-linkable functional group and an acrylic oligomer containing 10 to 40 percent by mole of vinyl monomer with a lactam ring through the use of a cross-linking agent, and wherein this medical tape is made by compounding the acrylic oligomer in the range of 50 to 700 parts by weight relative to 100 parts by weight of acrylic polymer, while the number average molecular weight of the acrylic polymer is set at a value within the range of 300,000 to 1,500,000, and the number average molecular weight of the acrylic oligomer is set at a value within the range of 1,000 to 10,000.

6 Claims, 2 Drawing Sheets

MEDICAL PRESSURE-SENSITIVE ADHESIVE COMPOSITION, PROCESS FOR PRODUCING THE SAME, AND MEDICAL TAPE

CROSS REFERENCE TO RELATED APPLICATIONS

This application is a continuation of U.S. Application Ser. No. 10/504,180, filed Aug. 10, 2004 now abandoned, which is a National Stage of International Application No. PCT/JP02/13695, filed Dec. 26, 2002.

TECHNICAL FIELD

The present invention relate to a medical pressure-sensitive adhesive composition, a process for producing the same, and a medical tape (adhesive tape). In particular, it relates to a medical pressure-sensitive adhesive composition having excellent re-adhesion property, and also excellence in both the peel adhesion property and the low skin stimulus property (low skin irritation), although the two are mutually contradictory. Also it relates to a process for producing the same, and a medical tape.

BACKGROUND ART

Since a medical tape (adhesive tape) which consists of a substrate and a medical pressure-sensitive adhesive composition is used by adhering or winding itself around the skin (corneous layer), as well as having moderate adhesion to the skin; it is preferable to have a proper peel property that does not cause skin stimulus or a rash by peeling damage to the corneous layer of the skin.

Therefore, in recent years, the medical pressure-sensitive adhesive composition and the medical tape have been proposed in consideration of a good balance between the skin adhesion property and the peel property.

For example, JP6-4533B(JP62-77316A) has disclosed the external application medicine component in which a polymer alloy is laminated on a substrate, wherein the polymer alloy has a number average molecular weight of 90,000 to 250,000 and the ratio (Mw/Mn) of a weight average molecular weight (Mw) to the number average molecular weight (Mn) of 6 to 12, and consists of 80 to 99.5 percent by weight of acrylic polymer and 0.5 to 20 percent by weight of acrylic oligomer having a number average molecular weight of 700 to 5,000.

Moreover, JP3-70685B has disclosed the pasting agent in which a pressure-sensitive adhesive layer containing a medicament and an (meta)acrylic acid ester-vinyl pyrrolidone random copolymer that contains 1 to 60 percent by mole of vinyl pyrrolidone is laminated on one surface of a substrate sheet.

However, each of the external application medicine component has been disclosed in JP6-4533B and JP3-70685B is substantially a single formulation, and moreover, because it is not cross-linked, it causes a shortfall of cohesive force or an excessive restriction of the additional amount of an acrylic oligomer, and the control of the corneous picking area ratio becomes difficult. Also, the problem of poor re-adhesion property is witnessed, as represented in the result of the comparison between comparative example 9 and the present invention as shown in FIG. 2. Moreover, since the number average molecular weight of the acrylics polymer to be used is low, the problem is witnessed in that the cohesive force becomes even more insufficient and the adhesion to the skin becomes poor.

Therefore, various acrylic adhesive compositions that contain an acrylic acid ester polymer and a liquid component or pasting agents including them have been known.

For example, JP5-139960A has disclosed the pasting agent, which has the adhesive layer made from the cross-linked polymer on one side of a substrate. This pasting agent is characterized by the 180° peel adhesion strength that is 20 to 180 g/12 mm in width, when the adhesive layer is bonded together. More concretely, this pasting agent contains an acrylic acid ester polymer and a liquid plasticizer which is compatible with this polymer, as an adhesive layer.

Moreover, JP2971998B (JP5-65460A) has disclosed the acrylic pressure sensitive adhesive sheet which has the maximal moving distance such as 0.5 to 6 times of the adhesion layer's thickness due to a shear deformation under shear stress, which contains acrylic acid ester polymer and a liquid component, for example, a plasticizer or a surfactant, which is compatible with the acrylic acid ester polymer on at least one surface of a support, and which is an elastic body that does not cause cohesive failure or interface failure when a shear stress is applied.

However, in the acrylic pressure-sensitive adhesive composition and the pasting agent including the same, which have been disclosed in the JP5-139960A and JP2971998B(JP 5-65460A), the problem is witnessed in that the re-adhesion property is poor, as represented in the result of the comparison between comparative example 11 and the present invention which are shown in FIG. 2. More concretely, since the compatibility between the acrylic polymer and the liquid component or a plasticizer that is added to the acrylic polymer is inadequate, the liquid component may migrate to the surface of the adhesion layer, and skin stimulus becomes high. On the other hand, the problem is witnessed in that proper peel adhesion strength is not obtained when the adhesion is tried again, after adhesion to the skin and peeling off have once been performed. Therefore, to solve the above problems, the inventors of the present invention have carried out several experimental studies on medical tapes including specific acrylic polymers and specific acrylic oligomers. As a result, the intermediate composition was prepared in advance; this composition was composed of an acrylic polymer having a predetermined number average molecular weight (Mn) including a predetermined amount of a specific type of acrylic oligomer having a predetermined number average molecular weight (Mn). Then, by crosslinking the intermediate composition, it was able to provide a medical tape that had an excellent re-adhesion property and that caused only slight skin stimulus, while at the same time, the wettability against the skin was kept high, and a predetermined peel adhesion strength was maintained. Consequently, the present invention has been completed.

Thus, an objective of the present invention is to provide a medical pressure-sensitive adhesive composition that is excellent in re-adhesion property, while the peel adhesion property is good and skin stimulus is low, to provide a process for producing the same, and to provide a medical tape in which such a medical pressure-sensitive adhesive composition is formed on a substrate.

SUMMARY OF THE INVENTION

[1] According to the present invention, a medical pressure-sensitive adhesive composition is provided, in which an intermediate composition is cross-linked through the use of a cross-linking agent, wherein the intermediate composition contains an acrylic polymer having a cross-linkable functional group and an acrylic oligomer prepared by polymerization of monomers containing 10 to 40 percent by weight of vinyl monomer with a lactam ring, while the number average molecular weight of the acrylic polymer is set at a value within the range of 300,000 to 1,500,000, the number average molecular weight of the acrylic oligomer is set at a value within the range of 1,000 to 10,000, and the medical pressure-sensitive adhesive composition is made by compounding the acrylic oligomer in the range of 50 to 700 parts by weight relative to 100 parts by weight of acrylic polymer. Consequently, the problem noted earlier can be solved.

That is, since a specific acrylic oligomer increases the wetting area against the skin, the predetermined peel adhesion strength can be obtained, while a medical pressure-sensitive adhesive composition exhibiting low skin stimulus and having an excellent re-adhesion property can be obtained. Moreover, since the number average molecular weight of the acrylic polymer to be used is comparatively high, and the acrylic polymer is cross-linked, a high cohesive force is obtained, a good compatibility with an acrylic oligomer is exhibited, peel adhesion strength is easily obtained, and the migration of the acrylic oligomer to the outside from the acrylic polymer can be prevented easily.

[2] Also, in the component of the medical pressure-sensitive adhesive composition of the present invention, it is preferable that an acrylic polymer having no cross-linkable functional group is included other than the acrylic polymer having a cross-linkable functional group, and the additional amount of this acrylic polymer is set at a value within the range of 1 to 50 percent by weight, relative to the whole amount of the medical pressure-sensitive adhesive composition.

[3] Also, in the component of the medical pressure-sensitive adhesive composition of the present invention, it is preferable that the acrylic oligomer contains a (meth)acrylic acid alkyl ester monomer as a monomer component, and the molar fraction of this (meth)acrylic acid alkyl ester monomer is set at a value within the range of 60 to 90 percent by mole relative to the whole amount of the oligomer.

[4] Also, in the medical pressure-sensitive adhesive composition of the present invention, it is preferable that the acrylic oligomer includes 2-ethylhexylacrylic ester and N-vinyl-2-pyrrolidone as monomer components.

[5] Also, in the medical pressure-sensitive adhesive composition of the present invention, it is preferable to set the viscosity (25° C.) of the acrylics oligomer at a value within the range of 10 to 1,000 dPa·s.

[6] Also, in the component of the medical pressure-sensitive adhesive composition of the present invention, it is preferable that a medicament is included at content within the range of 0.1 to 30 percent by weight relative to the whole amount of medical pressure-sensitive adhesive composition.

[7] Moreover, an another embodiment of the present invention is a process for producing a medical pressure-sensitive adhesive composition including the following steps (1) to (4);

(1) a step to prepare an acrylic polymer that has a number average molecular weight of 300,000 to 1,500,000 and has a cross-linkable functional group (2) a step to prepare an acrylics oligomer which has a number average molecular weight of 1,000 to 10,000 and in which monomer components containing 10 to 40 percent by mole of vinyl monomer with a lactam ring are polymerized (3) a step to prepare an intermediate composition by compounding an acrylic oligomer within the range of 50 to 700 parts by weight relative to 100 parts by weight of acrylic polymer (4) a step to add a cross-linking agent into the intermediate composition obtained from the step (3) so as to carry out the cross-linking Thus, by carrying out the production process in this way, the wetting area increases against the skin and a predetermined peel adhesion strength is obtained, while a medical pressure-sensitive adhesive composition exhibiting low skin stimulus and having an excellent re-adhesion property is obtained efficiently, since the mixing and dispersion of the acrylic polymer and the acrylic oligomer becomes easy and uniformly.

[8] Also, an another embodiment of the present invention is a medical tape in which a medical pressure-sensitive adhesive composition is laminated on a substrate, wherein the medical pressure-sensitive adhesive composition is prepared by cross-linking an intermediate composition containing an acrylic polymer having a cross-linkable functional group and an acrylic oligomer prepared by polymerization of monomers containing 10 to 40 percent by mole of vinyl monomer with a lactam ring through the use of a cross-linking agent. This medical tape is made by compounding the acrylic oligomer in the range of 50 to 700 parts by weight relative to 100 parts by weight of acrylic polymer, while the number average molecular weight of the acrylic polymer is set at a value within the range of 300,000 to 1,500,000, and the number average molecular weight of the acrylic oligomer is set at a value within the range of 1,000 to 10,000.

By constituting the medical tape like this, an excellent wettability against the skin is exhibited, a predetermined peel adhesion strength is obtained, while the skin stimulus is low, and an excellent re-adhesion property is exhibited. Furthermore, since it is easy to relatively adjust the peel adhesion strength and the cohesive force, the transfer of the acrylic oligomer to the backside of the substrate can be easily prevented.

DESCRIPTION OF THE PREFERRED EMBODIMENTS

Figure 1:
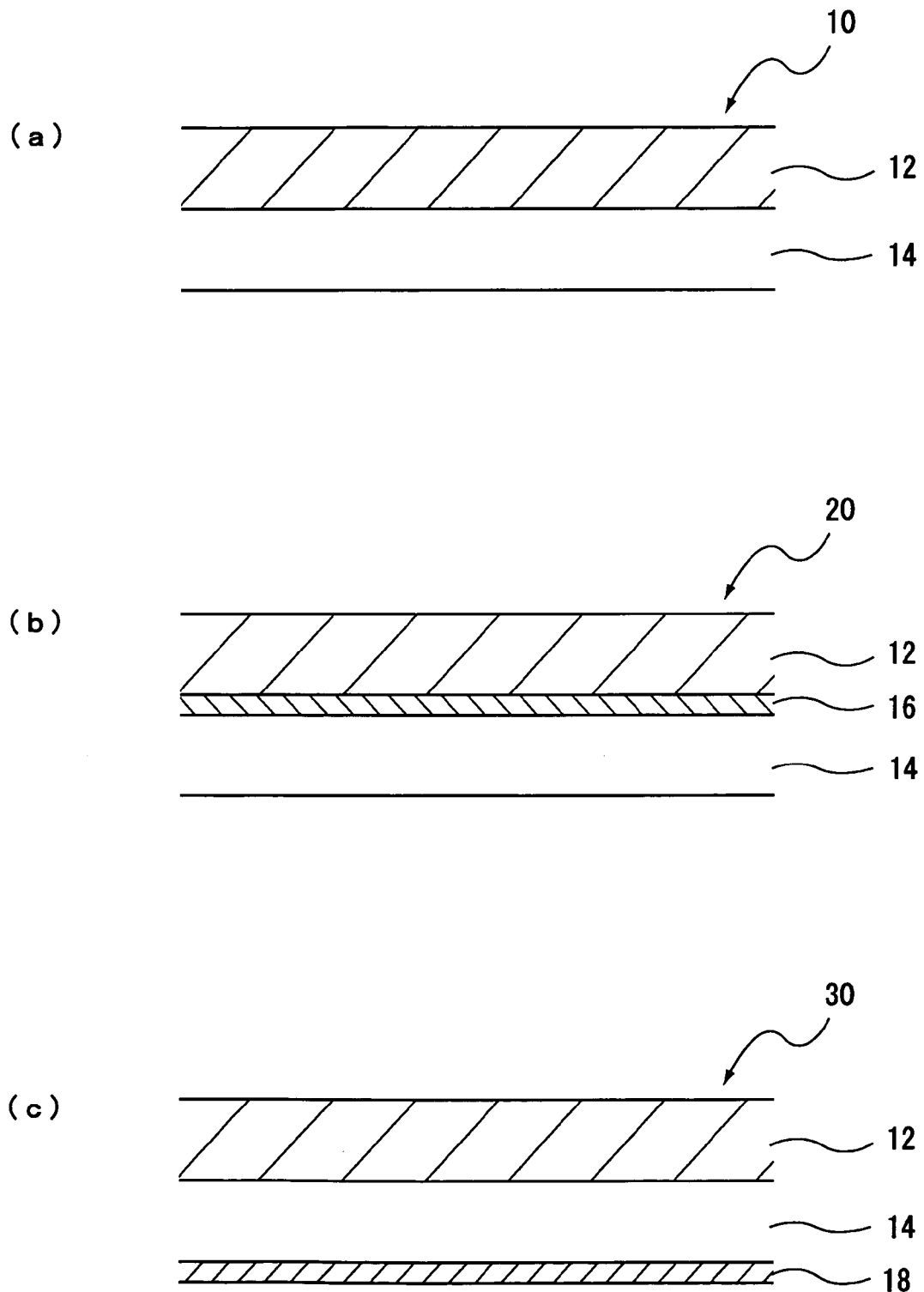
FIG. 1 is a diagram that illustrates the example of the medical tape according to the present invention.

Referring to each appropriate diagram, the preferred embodiments of the medical pressure-sensitive adhesive composition, the medical tape and the like according to the present invention will be specifically described.

First Embodiment

The first embodiment is a medical pressure-sensitive adhesive composition in which an intermediate composition is cross-linked through the use of a cross-linking agent, wherein the intermediate composition contains an acrylic polymer having a cross-linkable functional group and an acrylic oligomer prepared by polymerization of monomers containing 10 to 40 percent by weight of vinyl monomer with a lactam ring, while the number average molecular weight of the acrylic polymer is set at a value within the range of 300,000 to 1,500,000, the number average molecular weight of the acrylic oligomer is set at a value within the range of 1,000 to 10,000, and the medical pressure-sensitive adhesive composition is made by compounding the acrylic oligomer in the range of 50 to 700 parts by weight relative to 100 parts by weight of acrylic polymer.

1. Acrylic Polymer Having a Cross-linkable Functional Group (1) Type

As for an acrylic polymer having a cross-linkable functional group, used in the pressure-sensitive adhesive composition of the present invention, as long as it is a polymer obtained by copolymerization or homopolymerization of the acrylic monomer containing the vinyl monomer having a cross-linkable functional group, the type is not particularly limited. For example, it is preferable to be an acrylic polymer obtained by copolymerization of the vinyl monomer functional groups, such as carboxyl groups or hydroxyl groups and (meth)acrylic acid alkyl ester with the alkyl group's carbon number of 1 to 14.

The reason for this is the acrylic polymer derived from such a monomer component is easily cross linked by an external cross linking agent, so as to improve its cohesive force, and also is mutually dissolved easily with a specific acrylic oligomer, so that the wetting area can be increased most effectively.

Moreover, examples of (meth)acrylic acid alkyl esters with the alkyl group's carbon number of 1 to 14 include (meth) acrylic acid methyl ester, (meth)acrylic acid ethyl ester, (meth) acrylic acid propyl ester, (meth)acrylic acid isopropyl ester, (meth)acrylic acid 2-methoxyethyl ester, (meth)acrylic acid butyl ester, (meth)acrylic acid isobutyl ester, (meth) acrylic acid pentyl ester, (meth)acrylic acid hexyl ester, (meth)acrylic acid octyl ester, (meth)acrylic acid isooctyl ester, (meth)acrylic acid 2-ethylhexyl ester, (meth)acrylic acid nonyl ester, (meth)acrylic acid isononyl ester, and (meth) acrylic acid lauryl ester alone or combinations of at least two thereof.

On the other hand, examples of vinyl monomers having a cross-linkable functional group include one of (meth)acrylic acid with carboxyl groups, or (meth)acrylic acid 2-hydroxyethyl ester with hydroxyl groups alone or combinations of at least two thereof.

Moreover, it is preferable to set the additional amount of compounding of the above-described monomer at a value within the range of 1 to 15 percent by weight the amount of the whole monomer components at the time of the polymerization.

The reason for this is when the additional amount of compounding of the above-described monomer becomes less than a value of 1 percent by weight, the cross-linking becomes insufficient and, therefore, the peel adhesion strength to the skin may not be improved. On the other hand, if the additional amount of compounding of the above-described monomer exceeds 15 percent by weight, the skin stimulus caused by medical pressure-sensitive adhesive composition may increase.

Furthermore, as for the acrylic polymer having a cross-linkable functional group, it is preferable to include at least one monomer component identical with that in the acrylic oligomer, which will be mentioned later on.

The reason for this is when the acrylic polymer and the acrylic oligomer are the same type of monomer component like this, the compatibility between the acrylic polymer and the acrylic oligomer improves remarkably.

(2) Number Average Molecular Weight (Mn)

It is preferable to set a number average molecular weight of acrylic polymer at a value within the range of 300,000 to 1,500,000.

The reason for this is, when the number average molecular weight of such an acrylic polymer becomes less than the value of 300,000, insufficiency of the internal cohesive force of the adhesive agent may occur, and sometimes a part of adhesive is left behind. On the other hand, when the number average molecular weight of such an acrylic polymer exceeds the value of 1,500,000, uniform mixing may become difficult and the stable properties may not be acquired.

Therefore, it is more preferable to set the number average molecular weight of this acrylic polymer at a value within the range of 500,000 to 1,500,000, and it is even more preferable to set at a value within the range of 700,000 to 1,000,000.

The acrylic polymer's number average molecular weight can be measured by using the Gel Permeation Chromatography (GPC) method.

(3) Glass Transition Temperature

Moreover, it is preferable to set the acrylic polymer's glass transition temperature (Tg1) at a value within the range of −70° C. to −10° C., and it is more preferable to set at a value within the range of −45° C. to −15° C.

The reason for this is when the acrylics polymer's glass transition temperature becomes less than −70° C., the medical pressure-sensitive adhesive composition may be easily transferred to the back of substrate, or the skin stimulus may be increased. On the other hand, when the acrylic polymer's glass transition temperature exceeds −10° C., the peel adhesion strength to the skin of the medical pressure-sensitive adhesive composition may be remarkably lowered.

The glass transition temperatures of this acrylic polymer and an acrylic oligomer that will be mentioned later may either be measured by using a Differential Scanning Calorimeter (DSC), or may also be calculated from the Fox formula.

(4) Aging Polymerization

Moreover, it is preferable that the acrylic polymer is subjected to aging polymerization through further addition of a polymerization initiator after the polymer is prepared by standard polymerization.

The reason for this is that the amount of remaining monomer in the medical pressure-sensitive adhesive composition may decrease remarkably by adding an extra polymerization initiator after once the standard polymerization is completed, so as to polymerize the remaining monomer efficiently. Therefore, skin stimulus that is caused by the remaining monomer entering into the skin with the acrylic oligomer can be effectively prevented.

So, it is preferable to set the second additional amount of the polymerization initiator at a value within the range of 1 to 30 percent by weight relative to the first additional amount of the polymerization initiator.

2. Acrylic Oligomer (1) Type

As a monomer component in the acrylic oligomer, a vinyl monomer, which has at least one lactam ring in the molecule, is used at content within the range of 10 to 40 percent by mole.

The reason for this is that by using the vinyl monomer, which has the lactam ring, the wetting area (S) against the skin is moderately increased, and a predetermined peel adhesion strength ($W = S \times F$) can easily be obtained without increasing the adhesion strength (F) per unit area specific to an pressure-sensitive adhesive. Moreover, if the oligomer contained this vinyl monomer, even if comparatively large quantities were added, it would not cause the acrylic polymer's cohesive force to fall excessively. As a result an excellent peel property from the skin can be exhibited. Furthermore, if the oligomer contained this vinyl monomer, the compatibility with the acrylic polymer increased, and when a medicament and additive agents were added to the medical pressure-sensitive adhesive composition, the medicaments and the like could be dispersed easily.

As for a suitable example of the vinyl monomer with such a lactam ring, a water-soluble vinyl monomer can be mentioned, but especially, examples thereof include N-vinyl-2-pyrrolidone, N-vinyl-2-piperidone, N-vinyl-ε-caprolactam, and the like alone or combinations of at least two thereof.

Moreover, the reason for setting the amount of the vinyl monomer with a lactam ring at a value within the range of 10 to 40 percent by mole is, if the amount of the vinyl monomer with the lactam ring becomes at a value below 10 percent by mole, the effect of increasing the wetting area against the skin may not be exhibited. On the other hand, when the amount of the vinyl monomer with such a lactam ring exceeds 40 percent by mole, the plasticization of acrylic pressure-sensitive adhesive polymer becomes inadequate, or its viscosity rises excessively, and thereby, uniform mixing with acrylic pressure-sensitive adhesive polymer may become difficult.

Therefore, it is more preferable to set the amount of the vinyl monomer with a lactam ring at a value within the range of 12 to 35 percent by mole relative to the amount of the whole monomer components.

Moreover, although except for the vinyl monomer with a lactam ring, the type of monomer component is not specifically limited. It is, however, preferable to use, for example, a (meth)acrylic acid alkyl ester with the alkyl group's carbon number of 2 to 14. Specific examples include (meth) acrylic acid ethyl ester, (meth) acrylic acid propyl ester, (meth) acrylic acid isopropyl ester, (meth)acrylic acid 2-methoxyethyl ester, (meth)acrylic acid butyl ester, (meth)acrylic acid isobutyl ester, (meth)acrylic acid pentyl ester, (meth)acrylic acid hexyl ester, (meth)acrylic acid octyl ester, (meth)acrylic acid isooctyl ester, (meth)acrylic acid 2-ethylhexyl ester, (meth)acrylic acid nonyl ester, (meth)acrylic acid isononyl ester, and (meth)acrylic acid lauryl ester alone or combinations of at least two thereof. Furthermore, as for the monomer component of this acrylic oligomer, the combination of (meth)acrylic acid 2-ethylhexyl ester and N-vinyl-2-pyrrolidone is preferable.

(2) Number Average Molecular Weight (Mn)

Moreover, it is preferable to set the number average molecular weight of acrylic oligomer at a value within the range of 1,000 to 10,000.

The reason for this is, when the number average molecular weight of such an acrylic oligomer becomes less than the value of 1,000, it becomes easy to penetrate inside the skin and the skin stimulus property of the medical pressure-sensitive adhesive composition may increase. On the other hand, if the number average molecular weight of such an acrylic oligomer exceeds 10,000, the plasticization of the acrylic adhesive agent polymer becomes inadequate, or the viscosity increases excessively, it becomes difficult to mix uniformly with the acrylic adhesive agent polymer, and furthermore, the wettability to the skin may be reduced.

Therefore, it is even more preferable to set the number average molecular weight of this acrylic oligomer at a value within the range of 1,200 to 7,000.

(3) Viscosity

Moreover, it is preferable to set the viscosity of the acrylic oligomer (measurement temperature: 25° C.) measured by a B type viscometer (Brookfield viscometer) at a value within the range of 10 to 1,000 dPa·s.

The reason for this is, when the acrylic oligomer's viscosity becomes less than the value of 10 dPa·s, it becomes easy to penetrate inside the skin and sometimes this may cause skin stimulus to increase. On the other hand, when the acrylic oligomer's viscosity exceeds 1,000 dPa·s, the plasticization of the acrylic adhesive agent polymer may become inadequate, or the viscosity may be excessively increased, it becomes difficult to mix uniformly with the acrylic adhesive agent polymer, and furthermore, the wettability to the skin may be reduced.

Therefore it is more preferable to set the acrylic oligomer's viscosity (measurement temperature: 25° C.) at a value within the range of 15 to 800 dPa·s, and it is even more preferable to set at a value within the range of 20 to 500 dPa·s.

(4) Additional Amount

Moreover, its distinctive feature is that the additional amount of the acrylic oligomer is within the range of 50 to 700 parts by weight, relative to 100 parts by weight of the acrylic polymer having a cross-linkable functional group. The reason for this is when the additional amount of acrylic oligomer is less than the value of 50 parts by weight, the wettability to the skin may be remarkably reduced. On the other hand, when the additional amount of acrylic oligomer exceeds 700 parts by weight, an excessive decrease in the cohesive force of the adhesive agent may occur, and a part of adhesive may be left on the skin or a predetermined peel adhesion strength may not be obtained. Therefore, it is more preferable to set the additional amount of the acrylic oligomer at a value within the range of 50 to 500 parts by weight relative to 100 parts by weight of the acrylic polymer having a cross-linkable functional group. In addition, as will be mentioned later on, in the case an acrylic polymer having no cross-linkable functional group is used together with the acrylic polymer having a cross-linkable functional group, it is more preferable to set the additional amount of the acrylic oligomer at a value within the range of 300 to 700 parts by weight relative to 100 parts by weight of the acrylic polymer having a cross-linkable functional group.

(5) Glass Transition Temperature

Moreover, it is preferable to set the glass transition temperature (Tg2) of an acrylic oligomer at a value within the range of −70° C. to −10° C. The reason for this is when the glass transition temperature of this acrylic oligomer becomes a value below −70° C., the acrylic oligomer may exude through, and the skin stimulus may increase. On the other hand, when the glass transition temperature of this acrylic oligomer exceeds −10° C., the wettability to the skin of the medical pressure-sensitive adhesive composition may be reduced.

(6) Production Process

Moreover, although the producing process for an acrylic oligomer is not particularly limited, it is preferable to carry out the polymerization (homopolymerization or copolymerization) of the acrylic monomer, while adjusting the number average molecular weight, using a predetermined amount of a chain transfer agent (Lauryl mercaptan, Mercaptoethanol, etc.), for example. To put it more specifically, it is preferable to produce, for example, by solution polymerization in which a solvent, such as ethyl acetate, is used and a predetermined amount of the chain transfer agent is added or by emulsion polymerization in which an aqueous solvent is used and a predetermined amount of the chain transfer agent is added.

3. Acrylic Polymer Having No Cross-linkable Functional Group (1) Type

It is preferable to use the acrylic polymer having no cross-linkable functional group together with the acrylic polymer having a cross-linkable functional group. That is, by using such acrylic polymers unitedly, the wettability against the skin can be improved without reducing cohesive force excessively.

Here, such an acrylic polymer having no cross-linkable functional group is a polymer containing no vinyl monomer having a cross-linkable functional group as a monomer component, and is preferably an acrylic polymer obtained by the polymerization of, for example, (meth)acrylic acid alkyl ester that has the alkyl group's carbon number of 1 to 14. More preferably, the acrylic polymer is obtained by the copolymerization of the vinyl monomer with a lactam ring at within the range of, for example, 1 to 40 percent by mole as in the acrylic oligomer.

(2) Number Average Molecular Weight (Mn) and Glass Transition Temperature

The number average molecular weight and the glass transition temperature of the acrylic polymer having no cross-linkable functional group are the same as that described above with respect to the acrylic polymer having a cross-linkable functional group.

(3) Additional Amount

In the case where the acrylic polymer having no cross-linkable functional group is used together with the acrylic polymer having a cross-linkable functional group, it is preferable to set the additional amount at a value within the range of 1 to 50 percent by weight relative to the whole amount of the medical pressure-sensitive adhesive composition. The reason for this is when this additional amount becomes less than the value of 1 percent by weight, the effect of the addition may not appear and the wettability against the skin may not improve. On the other hand, when the additional amount exceeds 50 percent by weight, the existence amount of the acrylic polymer having a cross-linkable functional group is decreased relatively, and as a result, the cohesive force may be reduced. Therefore, it is more preferable to set the additional amount of the acrylic polymer having no cross-linkable functional group at a value within the range of 5 to 40 percent by weight against the whole amount of the medical pressure-sensitive adhesive composition, and it is even more preferable to set at a value within the range of 10 to 35 percent by weight.

4. Cross-linking Agent

Moreover, it is preferable to cross-link by adding a cross-linking agent into the intermediate composition that includes an acrylic polymer and an acrylic oligomer. That is, for example, it is preferable to add the cross-linking agent of 0.01 to 15 percent by weight relative to the amount of the whole intermediate composition, in order to adjust the cohesive force of the acrylic polymer. The reason for this is when the additional amount of such a cross-linking agent becomes less than the value of 0.01 percent by weight, a part of adhesive may be left behind because of inadequacy of the cross-linking. On the other hand, when the additional amount of such a cross-linking agent exceeds 15 percent by weight, the wettability to the skin may be remarkably reduced because of excessive cross-linking. Therefore, it is more preferable to set the additional amount of such a cross-linking agent at a value within the range of 0.05 to 8 percent by weight relative to the amount of the whole intermediate composition, and it is even more preferable to set at a value within the range of 0.1 to 5 percent by weight. In addition, as preferable sorts of cross-linking agent, for example, polyvalent epoxy compounds, such as ethylene glycol-diglycidyl ether and triglycidyl isocyanurate, polyvalent isocyanate compounds as addition derivatives of tolylene diisocyanate or hexamethylene diisocyanate, polyvalent aziridine compounds, polyvalent metal chelate compounds, and the like can be listed.

5. Additive Agent (1) Medicament

Moreover, a medicament can be added as an additive agent so that a predetermined effect of the medicament can work in the medical pressure-sensitive adhesive composition. The type of medicament is not particularly limited, and example thereof may include anti-inflammatory agent, anti-inflammatory anodyne, coronary vasodilators, asthma, antihypertensive agent, anti-histaminic, tranquilizer, anti-biotic, anesthetic, vitamin preparation, and the like alone or combinations of at least two thereof. Moreover, although the additional amount of the medicament varies depending on the type of medicament, or the usage of the medical pressure-sensitive adhesive composition, and for example, it is preferable to set it at a value within the range of 0.1 to 30 percent by weight relative to the amount of the whole medical pressure-sensitive adhesive composition.

(2) Other Additive Agents

Moreover, it is preferable to add various additive agents in the medical pressure-sensitive adhesive composition. Examples thereof include an anti-oxidant, a viscosity control agent, a UV absorber, a hiding agent, a plasticizer, wax, a coloring agent, an inorganic filler, an organic filer, an expander, a coupling agent and the like alone or combinations of at least two thereof.

6. Corneous Picking Area Ratio

Moreover, in the peeling test with respect to the skin as shown in example 1, it is preferable to set the corneous picking area ratio at a value of less than 30 percent. The reason for this is when such a corneous picking area ratio exceeds 30 percent, the skin stimulus becomes excessively high, and this may cause discomfort at the time of use or may excessively lower the re-adhesion property. However, if the corneous picking area ratio becomes excessively small, the type of acrylic monomer that can be used for the acrylic oligomer or the acrylic polymer may be restricted excessively. Therefore, it is more preferable to set the corneous picking area ratio at a value within the range of 0.1 to 20 percent and it is even more preferable to set the value within the range of 0.5 to 5 percent.

7. Waterdrop Contact Angle

Moreover, as for the detailed waterdrop contact angle shown in example 1, it is preferable to set this water drop contact angle at a value within a range of 10° to 700°. The reason for this is when the waterdrop contact angle is decreased to the value of less than 10°, skin stimulus may become excessively high and this may cause discomfort at the time of use. On the other hand, if this waterdrop contact angle exceeds 70°, the type of acrylic monomer that can be used for the acrylic oligomer or the acrylic polymer may be excessively restricted. Therefore, it is more preferable to set the waterdrop contact angle at a value within the range of 12° to 50°, it is even more preferable to set at a value within the range of 15° to 40°.

8. Production Process

Moreover, although the production process for the medical pressure-sensitive adhesive composition is not particularly limited, it is preferable to refer to the following production steps (1) to (4), for example. When it is carried out like this, the mixing and dispersion of the acrylic polymer and the acrylic oligomer become more easily, and the medical pressure-sensitive adhesive composition having an excellent re-adhesion property can be obtained efficiently.

(1) a step to prepare the acrylic polymer that has a number average molecular weight of 300,000 to 1,500,000 and has cross-linkable functional groups (2) a step to prepare the acrylic oligomer that has a number average molecular weight of 1,000 to 10,000 produced by polymerization of monomer components containing 10 to 40 percent by mole of vinyl monomer with a lactam ring (3) a step to prepare an intermediate composition by compounding an acrylic oligomer within the range of 50 to 700 parts by weight relative to 100 parts by weight of the acrylic polymer (4) a step to cross-link the intermediate composition by adding the cross-linking agent In addition, it is also preferable that the acrylic polymer having no cross-linkable functional group is prepared by polymerization in advance and if required, the step of adding and mixing the resultant polymer to the intermediate composition is carried out or the step of further adding and mixing the medicament and the additive agent is carried out.

Second embodiment

As illustrated in FIG. 1(a), the second embodiment is a medical tape 10 in which a medical pressure-sensitive adhesive composition 12 is laminated on a substrate 14, wherein the medical pressure-sensitive adhesive composition is prepared by cross-linking an intermediate composition containing an acrylic polymer having a cross-linkable functional group and an acrylic oligomer prepared by polymerization of monomers containing at least a vinyl monomer with a lactam ring through the use of a cross-linking agent, and the medical pressure-sensitive adhesive composition is obtained by incorporating 100 parts by weight of the acrylics polymer having the number average molecular weight at a value within the range of 300,000 to 1,500,000, and 50 to 700 parts by weight of the acrylics oligomer having the number average molecular weight at a value within the range of 1,000 to 10,000.

1. Substrate (1) Type

The type of substrate is not particularly limited, and examples thereof include a polyurethane film, a polyester film, a polyvinyl chloride film, a polyolefin film, a polycarbonate film, a polysulfone film, a polyphenylene sulfide film, a polyimide film, a paper, a film containing glass fiber, and the like.

In addition, the form of the substrate is not particularly limited as well; and for example, mesh-type or even fabrics or nonwoven fabrics are favorable.

(2) Thickness

Moreover, it is preferable to set the thickness of the substrate shown in FIGS. 1(a) to (c) at a value within the range of 5 to 2,000 μm. The reason for this is when the thickness of such a substrate is less in value than 5 μm, the mechanical strength is reduced and it may not be suitable for the use in the medical adhesive tape. On the other hand, when the thickness of this substrate exceeds 2,000 μm, the handling becomes difficult because of the excessive thickness, and also when the medical adhesive tape is made, it may easily peel off the skin and the like. Therefore, it is more preferable to set the thickness of the substrate at a value within the range of 10 to 1,000 μm, and it is even more preferable to set at a value within the range of 20 to 500 μm.

(3) Primer Layer

As shown in FIG. 1(b), it is preferable to form a primer layer 16 (including a sizing layer) on the surface of the substrate 14. By constituting like this, the adhesion strength between the substrate 14 and the adhesive agent layer 12, which consists of a medical pressure-sensitive adhesive composition can be increased, and the transfer of the medical pressure-sensitive adhesive composition to the backside of the substrate can be effectively prevented. In addition, as for such a primer layer, it is preferable to constitute from an acrylic resin, an epoxy resin and the like.

(4) Releasing Layer

As shown in FIG. 1(c), it is preferable to form a releasing layer 18 on the surface of the substrate 14 opposite to the side where the medical pressure-sensitive adhesive composition is formed. By constituting like this, not only rolling out from the roll type medical adhesive tape becomes easy, but also the transfer of the medical pressure-sensitive adhesive composition to the backside of the substrate can be prevented effectively. In addition, it is preferable to constitute such a releasing layer treated with a silicone resin or a long-chain alkyl compound, for example.

2. Medical Pressure-sensitive Adhesive Composition

Since the same medical pressure-sensitive adhesive composition as described in the first embodiment can be used here, the explanation thereof will not be provided.

3. Production Process

Although the production process for the medical tape is not limited, the tape can be produced easily by uniformly applying the medical pressure-sensitive adhesive composition to the substrate, by using a roll coater, a comma coater, a knife coater, and such, for example.

4. Peel Adhesion Strength

Moreover, it is preferable to set the peel adhesion strength (mode: 180° peel-off, substrate: phenolic resin plate, peeling speed: 300 mm/min) of the medical tape having the adhesive layer that consists of an medical pressure-sensitive adhesive composition in accordance with JIS Z0237 at the value within the range of 50 to 250 cN/12 mm. The reason for this is when such peel adhesion strength is less than 50 cN/12 mm, the tape may peel-off too easily from the skin and the function as a medical adhesive tape may become poor.

On the other hand, if this peel adhesion strength exceeds 250 cN/12 mm, it may become difficult to remove the medical pressure-sensitive adhesive composition from the skin and skin stimulus may become excessive and cause discomfort during use. Therefore, it is more preferable to set at a value within the range of 60 to 200 cN/12 mm, and it is even more preferable to set at a value within the range of 80 to 150 cN/12 mm. In addition, it is also preferable to adjust the peel adhesion strength of the medical tape by applying the medical pressure-sensitive adhesive composition with a pattern coating method instead of applying it all over the substrate surface.

EXAMPLES

The examples of the present invention are explained in detail hereafter. However, needles to say, the following explanation only exemplifies the present invention and the scope of the present invention should not be limited by these descriptions in anymore.

Example 1

1. Production Process for Medical Pressure-sensitive Adhesive Composition and Medical Tape (1) Preparation of an Acrylic Oligomer A monomer mixture solution was prepared by uniformly dissolving 20.5 g (0.185 mol, mixture mole fraction: 12 percent by mole) of N-vinyl-2-pyrrolidone, 250 g (1.356 mol, mixture mole fraction: 88 percent by mole) of acrylic acid 2-ethylhexyl ester, and 18.2 g (0.09 mol) of Lauryl mercaptan as a chain transfer agent into 73 g of ethyl acetate as a solvent. 0.5 g of azobisisobutyronitrile (AIBN) was added as a polymerization initiator after laying this monomer mixed solution in a polymerization reactor equipped with an agitator and a vapor condensation reflux tower. Subsequently, after agitating was further performed until the monomer mixed solution becomes homogeneous, the polymerization reactor was immersed in a hot water bath at 60° C., and solution polymerization was started. The polymerization reaction was continued for about 6 hours, while controlling the temperature of polymerization reactive solution at 65° C.±50° C. Subsequently, polymerization reaction solution was taken out from the polymerization reactor, and when the concentration (nonvolatile content) of the obtained acrylic oligomer was measured by the dry weight method (150° C., 1 hour), it was 80.4 percent by weight. Moreover, the obtained polymerization reaction solution was heated to 85° C. under decompression of 1 mmHg, the ethyl acetate serving as a solvent was removed, and the viscous acrylic oligomer was obtained. When the viscosity of the obtained acrylic oligomer was measured by using a B type viscometer, it was 65 dPa·s (measurement temperature: 25° C., the same holds true in the following description), and the number average molecular weight measured by using the GPC method (the same holds true in the following description) was 3,200.

(2) Preparation of Acrylic Polymer Having a Cross-linkable Functional Group

A monomer mixed solution was prepared by dissolving 10 g (5.5 parts by weight) of acrylic acid and 180 g (100 parts by weight) of acrylic acid 2-ethylhexyl ester into 232 g of ethyl acetate. Subsequently, the obtained monomer mixed solution was put into the polymerization reactor equipped with a vapor condensation reflux tower and an agitator, after adding 0.14 g of AIBN as a polymerization initiator, immersion into a hot water bath at 58° C., and the solution polymerization was started. The solution polymerization was continued for about 3 hours, while controlling the temperature of the polymerization solution at 65° C.±5° C. In addition, at the stage where an exothermic reaction had mostly ended, the temperature was raised up to 70° C.±2° C. after 0.04 g of AIBN was added again, the heating procedure was continued for about 5 hours, so that the polymerization reaction was completed. Subsequently, the polymerization reaction solution was taken out of the polymerization reactor and the concentration (nonvolatile content) of the obtained acrylic polymer was measured by the dry weight method (150° C., 1 hour), and the result was 45.5 percent by weight. Moreover, the solution viscosity of the obtained acrylic polymer (viscosity of an ethyl acetate solution measured by using a B type viscometer, the same holds true in the following description) was measured, and the result was 35 dPa·s. The number average molecular weight, which was measured by the GPC method, was 750,000.

(3) Cross-linking and Lamination Step

An intermediate composition was prepared by mixing 85 g of the resultant acrylic oligomer and 100 g (45.5 g in terms of acrylic polymer) of the acrylic polymer in an ethyl acetate solution. 3 g of polyvalent isocyanate compound (Nippon Polyurethane Industry Co. Ltd., Coronate-HL) serving as a reactive cross-linking agent was added into the intermediate composition. Afterwards, ethyl acetate was further added for concentration adjustment, and the medical pressure-sensitive adhesive composition (ethyl acetate solution) which had a nonvolatile residue content of 50 percent by weight, was obtained. The content of the acrylic oligomer in this medical pressure-sensitive adhesive composition was 65 percent by weight. Subsequently, after the medical pressure-sensitive adhesive composition was uniformly laminated on the polyester nonwoven fabric (200 μm in thickness) treated by sizing process to prevent the permeability to the backside, drying procedure was carried out by heating at 110° C., so that a medical tape (adhesive plaster) with an adhesion layer having a thickness of 40 μm was prepared.

2. Evaluation (1) Peel Adhesion Strength

The peel adhesion strength of the obtained medical tape was measured in accordance with JIS Z0237. The obtained result is shown in Table 1.

(2) Corneous Picking Area Ratio

The obtained medical tape was cut into strip specimens (width: 12 mm, length: 40 mm, effective adhesion area: 480 mm$^2$), and the resultant specimens were applied to the five-evaluator's inner skin of the upper arm. Afterwards, the specimens were peeled off after being applied for 24 hours respectively. Subsequently, the surface of the adhesion layer of the peeled medical tape was dyed with a dye solution (Gentian Violet and Brilliant Green), and the corneous layer that adhered to the surface of the adhesion layer by the peeling failure became dark purple color. By the image analysis method through the microphotograph, the coloring area ratio of the corneous layer (total of the area which was colored in dark purple/adhesion layer area×100) was measured as a corneous picking area ratio. The obtained result is shown in Table 1.

(3) Re-adhesion Property

The obtained medical tape was cut into strip specimens (width: 12 mm, length: 100 mm, effective adhesion area: 1,200 mm$^2$), and the specimen was applied to a person's skin on the upper back. Then, peel adhesion strength was measured as shown in the above (1) after the specimen was held intact for 20 minutes and was peeled off. This operation was repeated 5 times in total, and the re-adhesion property was evaluated. The obtained result is shown in Table 2.

Figure 2:
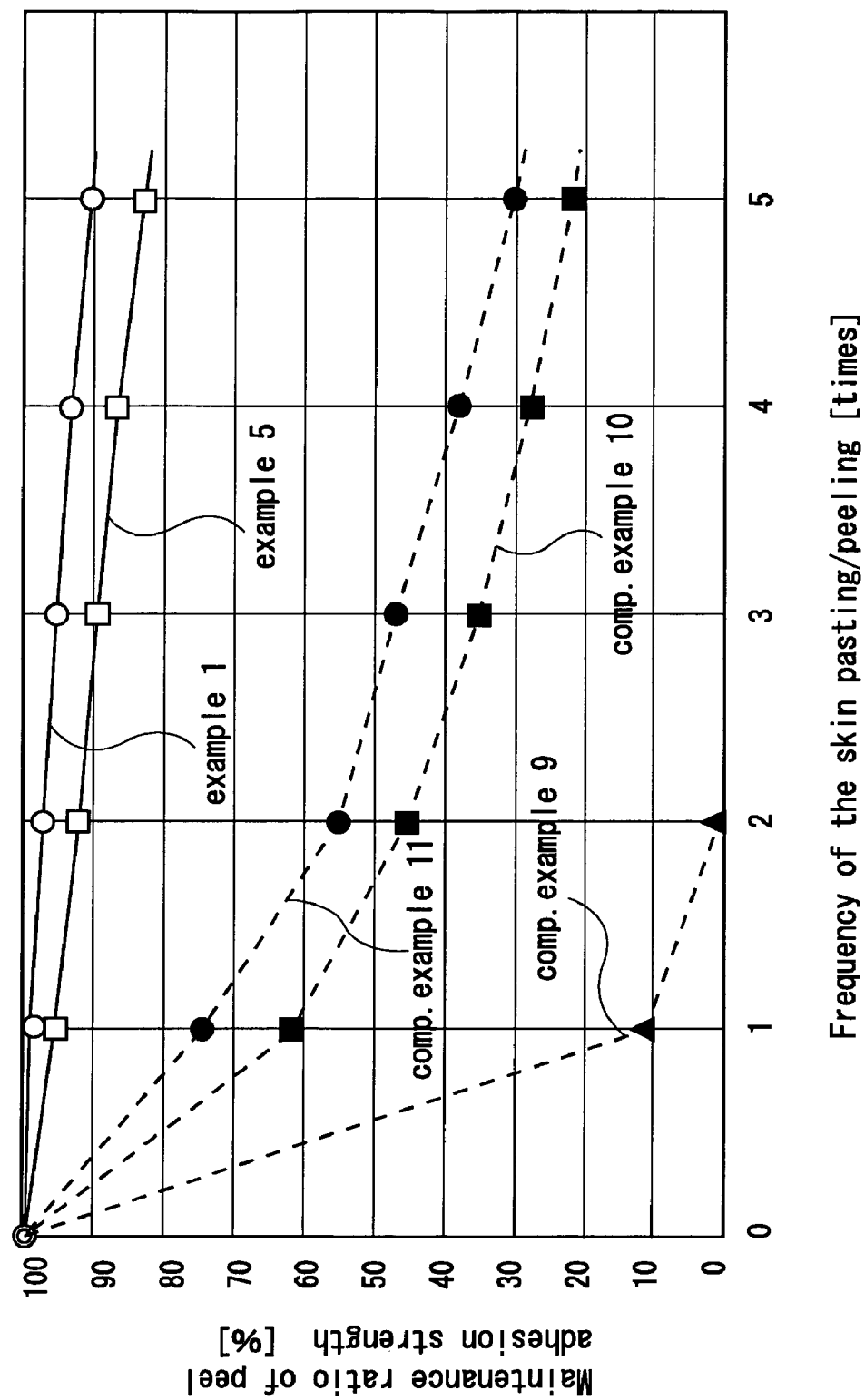
FIG. 2 is a diagram that illustrates re-adhesion property (the relationship between the number of times of the peeling off and the maintenance ratio of the peel adhesion strength).

In addition, with regard to the re-adhesion property, a relation between the frequency of the skin pasting/peeling and the maintenance ratio of peel adhesion strength (percent) are shown in FIG. 2 based on the result shown in Table 2. If the value of the peel adhesion strength (maintenance ratio of peel adhesion strength) is at least 50 percent of the initial peel adhesion strength after repeating at least five times, the practicality is excellent. Furthermore, if the value is 80 percent or more, it can be adhered practically many more times and this proves the outstanding practicality.

(4) Waterdrop Contact Angle

The waterdrop contact angle (measurement temperature: 25° C.) in the adhesion layer surface of the obtained medical tape was measured by using a contact angle measurement apparatus (made by Masuda Corporation). The obtained result is shown in Table 1.

(5) Unstuck Tendency, Skin Stimulus Tendency, and Adhesive Left Tendency

The obtained medical tape was processed into strip specimens (width: 12 mm, length: 40 mm, effective adhesion area: 480 mm$^2$). After pasting the specimens to the inner skin of the upper arm of the five evaluators for 24 hours, the tendencies for unstuck, skin stimulus, and adhesive left were evaluated based on the following standards, respectively. The obtained result is shown in Table 1.

(Unstuck Tendency)
Very good: All of the five people did not experience the specimen coming unstuck.
Good: Four or more people did not experience the specimen coming unstuck.
Fair: Three or more people did not experience the specimen coming unstuck.
Bad: Three or more people experienced the specimen coming unstuck.

(Skin Stimulus Tendency)
Very good: There was no skin stimulus at all according to the average experience of the five people.
Good: There was almost no skin stimulus according to the average experience of the five people.
Fair: There was slight skin stimulus according to the average experience of the five people.
Bad: There was notable skin stimulus according to the average experience of the five people.

(Adhesive Left Tendency)

Very good: There was no adhesive left according to the average experience of the five people.

Good: There was almost no adhesive left behind according to the average experience of the five people.

Fair: There was slight adhesive left according to the average experience of the five people.

Bad: There was remarkable adhesive left according to the average experience of the five people.

Examples 2 to 4

As shown in Table 1, the medical tape was made and evaluated like the example 1, except to change the monomer composition and the additional amount within the limits of the present invention. Consequently, in each, while proper peel adhesion strength to the skin is shown, the corneous picking area ratio is at a very low value. And at the same time, it becomes clear that it is possible to have a medical tape that has excellent re-adhesion property.

TABLE 1

|  |  |  | Example 1 | Example 2 | Example 3 | Example 4 |
|---|---|---|---|---|---|---|
| Acrylic Oligomer A | Charge (g) | 2EHA | 250 | 250 | 250 | 170 |
|  |  | NVP | 20.5 | 81.9 | 20.5 | 99 |
|  |  | 2MEA | — | — | — | 150 |
|  |  | LM | 18.2 | 67.1 | 9.1 | 42.4 |
|  | Viscosity (dPa · Sec) |  | 65 | 21 | 320 | 125 |
|  | Number Average Molecular Weight |  | 3200 | 1200 | 6200 | 2200 |
|  | Molar Fraction of NVP (%) |  | 12.0 | 35.2 | 12.0 | 30.1 |
|  | Glass Transition Temperature (Tg2, °C.) |  | −41.5 | −18.6 | −41.0 | −20.2 |
| Crosslinkable acrylic polymer B | Charge(g) | 2EHA | 180 | 180 | 180 | 375 |
|  |  | MMA | — | — | — | 125 |
|  |  | AA | 10 | 10 | 10 | 25 |
|  | Number Average Molecular Weight |  | 750000 | 750000 | 750000 | 910000 |
|  | Glass Transition Temperature (Tg1, °C.) |  | −45.3 | −45.3 | −45.3 | −20.6 |
| PSA | Additional amount (g) | Acrylic Oligomer A | 85.0 | 45.5 | 45.5 | 16.4 |
|  |  | Crosslinkable Acrylic Polymer B | 45.5 | 45.5 | 45.5 | 30.4 |
|  |  | Reactive Crosslinking Agent | 3.0 | 2.0 | 1.8 | 1.6 |
|  |  | Weight Ratio A/B × 100 | 187 | 100 | 100 | 54 |
| Evaluation | Peel Adhesion Strength (cN/12 mm) |  | 101 | 88 | 107 | 118 |
|  | Corneous sticking area ratio (%) |  | 0.7 | 0.9 | 1.8 | 3.2 |
|  | Waterdrop Contact Angle (°) |  | 41 | 22 | 44 | 28 |
|  | Unstuck Tendency |  | Very good | Very good | Very good | Very good |
|  | Paste left Tendency |  | Very good | Very good | Very good | Very good |
|  | Skin Stimulus Tendency |  | Very good | Very good | Very good | Very good |

2EHA: Acrylic acid 2-ethylhexyl ester
NVP: N-vinyl-2-pyrrolidone
2MEA: Acrylic acid 2-methoxyethyl ester
LM: Lauryl mercaptan
MMA: Methacrylic acid methyl ester
AA: Acrylic acid

TABLE 2

| Peel Adhesion Strength (cN/12 mm) | The frequency of the skin pasting | | | | | |
|---|---|---|---|---|---|---|
| | 0 time | 1 time | 2 times | 3 times | 4 times | 5 times |
| Example 1 | 102 | 100 | 99 | 98 | 95 | 93 |
| Example 5 | 108 | 103 | 98 | 96 | 95 | 90 |
| Comp. Example 9 | 255 | 30 | 0 | — | — | — |
| Comp. Example 10 | 146 | 90 | 65 | 48 | 42 | 32 |
| Comp. Example 11 | 150 | 112 | 82 | 69 | 58 | 46 |

Example 5

1. Production Process for the Medical Pressure-sensitive Adhesive Composition and the Medical Tape (1) Preparation of an Acrylic Oligomer Based on example 1, an acrylic oligomer liquid was obtained by a combination as shown in table 3. The viscosity of the obtained acrylic oligomer was 390 dPa·s, and the number average molecular weight was 3,200.

(2) Preparation of the Acrylic Polymer Having a Cross-linkable Functional Group

A monomer mixed solution was prepared by dissolving 20 g (11 parts by weight) of acrylic acid and 180 g (100 parts by weight) of acrylic acid 2-ethylhexyl ester into 300 g of ethyl acetate. Subsequently, the obtained monomer mixed solution was put in the polymerization reactor equipped with a vapor condensation reflux tower and an agitator, and after 0.15 g of AIBN as a polymerization initiator, immersion into a hot water bath at 58° C. was performed, and the solution polymerization was started. The solution polymerization was continued for about 3 hours, while controlling the temperature of the polymerization liquid at 65° C.±5° C. In addition, at the stage where an exothermic reaction had mostly ended, the temperature was raised up to 70° C.±2° C. after 0.04 g of AIBN was added again, the heating procedure was continued for about 5 hours, so that the polymerization reaction was completed. Subsequently, the polymerization reaction solution was taken out of the polymerization reactor and the concentration (nonvolatile content) of the obtained acrylic polymer was measured by the dry weight method (150° C., 1 hour), and the result was 40.7 percent by weight. Moreover, the solution viscosity of the obtained acrylic polymer was 55 dPa·s, and the number average molecular weight was 820,000.

(3) Preparation of the Acrylic Polymer Having No Cross-linkable Functional Group A monomer mixture solution was formed by dissolving 36.7 g of N-vinyl-2-pyrrolidone and 140 g of acrylic acid 2-ethylhexyl ester into 265 g of ethyl acetate. Subsequently, the obtained monomer mixed solution was put in the polymerization reactor equipped with a vapor condensation reflux tower and an agitator, after adding 0.13 g of AIBN as a polymerization initiator, immersion into a hot water bath at 58° C., and the solution polymerization was started. The solution polymerization was continued for about 3 hours, while controlling the temperature of the polymerization liquid at 65° C.±5° C. In addition, at the stage where an exothermic reaction had mostly ended, the temperature was raised up to 70° C.±2° C. after 0.035 g of AIBN was added again, the heating procedure was continued for about 5 hours, so that the polymerization reaction was completed. Subsequently, the polymerization reaction solution was taken out of the polymerization reactor and the concentration of the obtained acrylic polymer was measured by the dry weight method, and the result was 41 percent by weight. Moreover, the solution viscosity of the obtained acrylic polymer was 360 dPa·s, and the number average molecular weight was 880,000.

(4) The Cross-linking and Laminating Process

An intermediate composition was prepared by mixing 60 g of the resultant acrylic oligomer, 23 g (9 g in terms of acrylic polymer) of an acrylic polymer solution having a cross-linkable functional group, and 48 g (20 g in terms of acrylic polymer) of an acrylic polymer solution having no cross-linkable functional group. 0.9 g of polyvalent isocyanate compound was added as a reactive cross-linking agent (manufactured by Nippon Polyurethane Industry Co. Ltd., Coronate-HL) to the intermediate composition. Afterwards, ethyl acetate was further added for adjustment, and the medical pressure-sensitive adhesive composition (ethyl acetate solution) which had a nonvolatile residue content of 50 percent by weight, was obtained. The content of the acrylic oligomer in this medical pressure-sensitive adhesive composition was 67 percent by weight. Subsequently, after the medical pressure-sensitive adhesive composition was uniformly laminated on the polyester nonwoven fabric (200 μm in thickness) that had been treated by sizing process to prevent the permeation to the backside, drying procedure was carried out by heating at 110° C., so that a medical tape (adhesive plaster) with an adhesion layer having a thickness of 40 μm was prepared.

2. Evaluation

With regard to the peel adhesion strength of the obtained medical tape and the corneous picking area ratio and the like, are estimated in the same way as in example 1. Consequently, as shown in Table 3 and in a part of FIG. 2, in each, while proper peel adhesion strength to the skin is shown, it becomes clear that it is possible to provide a medical tape which has very fine re-adhesion property (maintenance ratio of peel adhesion strength).

TABLE 3

| | | | Example 5 | Example 6 |
|---|---|---|---|---|
| Acrylic Oligomer A | Charge (g) | 2EHA | 250 | 250 |
| | | NVP | 64.6 | 64.6 |
| | | LM | 21.2 | 21.2 |
| | Viscosity (dPa · Sec) | | 390 | 390 |

TABLE 3-continued

|  |  |  | Example 5 | Example 6 |
|---|---|---|---|---|
|  | Number Average Molecular Weight |  | 3200 | 3200 |
|  | Molar Fraction of NVP (%) |  | 30.0 | 30.0 |
|  | Glass Transition Temperature (Tg2, ° C.) |  | −24.6 | −24.6 |
| Crosslinkable | Charge (g) | 2EHA | 180 | 180 |
| acrylicpolymer B |  | AA | 20 | 20 |
|  | Number Average Molecular Weight |  | 820000 | 820000 |
|  | Glass Transition Temperature (Tg1, ° C.) |  | −45 | −45 |
| Non-cross linkable | Charge (g) | 2EHA | 140 | 140 |
| acrylic polymer C |  | NVP | 36.7 | 42.1 |
|  | Number Average Molecular Weight |  | 880000 | 840000 |
|  | Glass Transition Temperature (Tg3, ° C.) |  | −19.4 | −17.6 |
| PSA | Additional | Acrylic Oligomer A | 60.0 | 40.0 |
|  | amount (g) | Crosslincable Acrylic Polymer B | 9 | 10 |
|  |  | Non-cross lincable Acrylic Polymer C | 20 | 20 |
|  |  | Reactive Cross linking Agent | 0.9 | 0.9 |
|  |  | Weight Ratio A/B × 100 | 667 | 400 |
| Evaluation | Peel Adhesion Strength (cN/12 mm) |  | 105 | 95 |
|  | Corneous sticking area ratio (%) |  | 0.8 | 1.1 |
|  | Waterdrop Contact Angle (°) |  | 18 | 33 |
|  | Unstuck Tendency |  | Very good | Very good |
|  | Paste left Tendency |  | Very good | Very good |
|  | Skin Stimulus Tendency |  | Very good | Very good |

2EHA: Acrylic acid 2-ethylhexyl ester
NVP: N-vinyl-2-pyrrolidone
LM: Lauryl mercaptan
AA: Acrylic acid Example 6

As shown in Table 3, within the limits of the present invention, except for changing the additional amount of the acrylic polymer having no cross-linkable functional group, the medical pressure-sensitive adhesive composition and the medical tape was created and evaluated in the same way as in example 5.

Comparative Examples 1 to 11

As shown in Table 4 and in a part of FIG. 2, in comparative examples 1 to 11, except for changing the monomer composition and the additional amount outside the limits of the present invention respectively, the medical tape was created and evaluated based on example 1.

Consequently, in comparative example 1, the cohesive failure of the adhesive agent was intense due to not adding the cross-linking agent, so that an evaluation test was unable to be carried out.

Also, in comparative example 2, since the number average molecular weight of the acrylic polymer having a cross-linkable functional group is too little, it becomes clear that the value of corneous picking area ratio is extremely high, and the peeling damage on the skin (corneous layer) is very large, for example.

Also, in comparative example 3, since the numeric average molecular weight of the acrylic oligomer is too little, it becomes clear that serious skin stimulus and notable itching occur, for example.

Also, in comparative example 4, since the number average molecular weight of the acrylic oligomer is too much, it becomes clear that, as an example, the value of corneous picking area ratio is high, and the peeling damage to the skin (corneous layer) is greater.

Also, in comparative example 5, due to the very small additional amount of acrylic oligomer, it becomes clear that, as an example, the value of corneous picking area ratio is high, and the peeling damage to the skin (corneous layer) is therefore greater.

Also, in comparative example 6, due to a greater additional amount of acrylic oligomer, cohesive failure of the adhesive agent was intense and an evaluation test was unable to be carried out.

Also, in comparative example 7, since the molar fraction of N-vinyl-2-pyrrolidone in an acrylic oligomer is too small, it becomes clear that the value of corneous picking area ratio is high, and then the peeling damage to the skin (corneous layer) is large as well, for example.

Also, in comparative example 8, since the molar fraction of N-vinyl-2-pyrrolidone in an acrylic oligomer is too high, it becomes clear that the value of corneous picking area ratio is high, and the peeling damage to the skin (corneous layer) is large as well, for example.

Also, in comparative example 9, due to no addition of the acrylic oligomer, it becomes clear that, as an example, the value of corneous picking area ratio is extremely high, and the re-adhesion property is poor, as shown in Table 2 and FIG. 2.

Also, in comparative example 10, due to not using a vinyl monomer having a lactam ring at all, for an acrylic oligomer it becomes clear, as an example, that the value of corneous picking area ratio is high, and the re-adhesion property is poor, as shown in Table 2 and FIG. 2.

Moreover, in comparative example 11, although the plasticizer is added, due to not adding the specific acrylic oligomer at all, it becomes clear, as an example, that the value of corneous picking area ratio is high, and the re-adhesion property is poor, as shown in Table 2 and FIG. 2.

TABLE 4

|  |  |  | Comp. Ex. 1 | Comp. Ex. 2 | Comp. Ex. 3 | Comp. Ex. 4 | Comp. Ex. 5 | Comp. Ex. 6 |
|---|---|---|---|---|---|---|---|---|
| Acrylics oligomer or liquid material A | Charge (g) | 2EHA | 250 | 250 | 250 | 250 | 250 | 250 |
| | | NVP | 20.5 | 20.5 | 81.9 | 20.5 | 81.9 | 20.5 |
| | | LM | 18.2 | 18.2 | 134 | 3.6 | 67.1 | 18.2 |
| | Viscosity (dPa · Sec) | | 65 | 65 | 4 | N.A. | 21 | 65 |
| | Number Average Molecular Weight | | 3200 | 3200 | 700 | 15000 | 1200 | 3200 |
| | Molar Fraction of NVP (%) | | 12.0 | 12.0 | 35.2 | 12.0 | 35.2 | 12.0 |
| | Glass Transition Temperature (Tg2, °C.) | | −41.5 | −41.5 | −18.6 | −41.0 | −18.6 | −41.5 |
| Cross linkable acrylic polimer B PSA | Charge (g) | 2EHA | 180 | 180 | 180 | 180 | 180 | 180 |
| | | AA | 10 | 10 | 10 | 10 | 10 | 10 |
| | Number Average Molecular Weight | | 750000 | 100000 | 750000 | 750000 | 750000 | 750000 |
| | Glass Transition Temperature (Tg1, °C.) | | −45.3 | −45.6 | −45.3 | −45.3 | −45.3 | −45.3 |
| | Additional amount (g) | Acrylic Oligomer A | 45.0 | 45.5 | 22.8 | 45.5 | 11.0 | 80.0 |
| | | Liquid Material | — | — | — | — | — | — |
| | | Cross linkable acrylic polimer B | 45.5 | 45.5 | 45.5 | 45.5 | 45.5 | 10.0 |
| | | Reaction Type Cross linking Agent | none | 2.0 | 1.5 | 1.8 | 1.6 | 1.2 |
| | | Weight Ratio A/B × 100 | 100 | 100 | 50 | 100 | 24 | 800 |
| Evaluation | Waterdrop Contact Angle (°) | | 35 | 39 | 31 | 47 | 75 | 36 |
| | Peel Adhesion Strength (cN/12 mm) | | * | 265 | 120 | 184 | 192 | * |
| | Unstuck Tendency | | | Very good | Very good | Very good | Very good | |
| | Paste left Tendency | | | Fair | Very good | Very good | Very good | |
| | Skin Stimulus Tendency | | | Bad | Bad | Bad | Bad | |
| | Corneous sticking area ratio (%) | | | 74 | 4.5 | 33 | 38 | |

|  |  |  | Comp. Ex. 7 | Comp. Ex. 8 | Comp. Ex. 9 | Comp. Ex. 10 | Comp. Ex. 11 |
|---|---|---|---|---|---|---|---|
| Acrylics oligomer or liquid material A | Charge (g) | 2EHA | 250 | 250 | — | 250 | MIP |
| | | NVP | 7.1 | 127 | — | — | — |
| | | LM | 26.0 | 76.0 | — | 25.3 | — |
| | Viscosity (dPa · Sec) | | 10 | N.A | — | 3.9 | 0.1 or less |
| | Number Average Molecular Weight | | 2200 | 1200 | — | 2200 | 271 |
| | Molar Fraction of NVP (%) | | 4.5 | 45.7 | — | — | — |
| | Glass Transition Temperature (Tg2, °C.) | | −47.0 | −4.8 | — | −50.2 | — |
| Cross linkable acrylic polimer B PSA | Charge (g) | 2EHA | 180 | 180 | 180 | 180 | 180 |
| | | AA | 10 | 10 | 10 | 10 | 10 |
| | Number Average Molecular Weight | | 750000 | 750000 | 750000 | 750000 | 750000 |
| | Glass Transition Temperature (Tg1, °C.) | | −45.3 | −45.3 | −45.3 | −45.3 | −45.3 |
| | Additional amount (g) | Acrylic Oligomer A | 45.5 | 45.5 | — | 45.5 | — |
| | | Liquid Material | — | — | — | — | 45.5 |
| | | Cross linkable acrylic polimer B | 45.5 | 45.5 | 45.5 | 45.5 | 45.5 |
| | | Reaction Type Cross linking Agent | 1.2 | 1.2 | 0.4 | 1.4 | 2.0 |
| | | Weight Ratio A/B × 100 | 100 | 100 | 0 | 100 | 100 |
| Evaluation | Waterdrop Contact Angle (°) | | 104 | 12 | 115 | 124 | 121 |
| | Peel Adhesion Strength (cN/12 mm) | | 166 | 174 | 253 | 150 | 147 |
| | Unstuck Tendency | | Very good | Very good | Very good | Very good | Very good |
| | Paste left Tendency | | Very good | Very good | Very good | Very good | Very good |
| | Skin Stimulus Tendency | | Bad | Fair | Bad | Fair | Fair |
| | Corneous sticking area ratio (%) | | 31 | 29 | 89 | 22 | 24 |

2EHA: Acrylic acid 2-ethylhexyl ester
NVP: N-vinyl-2-pyrrolidone
LM: Lauryl mercaptan
MIP: Myristicacid isopropyl
AA: Acrylic acid
*Since cohesive failure of an adhesive agent was intense, an evaluation test could not be carried out.

INDUSTRIAL APPLICABILITY

According to the present invention, the intermediate composition is prepared earlier on, and the intermediate composition is prepared by adding a predetermined amount of specific type of acrylic oligomer having a predetermined number average molecular weight (Mn) to the acrylic polymer which has cross-linkable functional groups and which also has a predetermined number average molecular weight (Mn). By crosslinking the intermediate composition, a medical pressure-sensitive adhesive composition and a medical tape that cause only low skin stimulus while having an excellent re-adhesion property can be prepared wherein the wettability against the skin is kept high and appropriate peel adhesion strength is maintained. Therefore, a suitable medical tape is provided, which can be repeatedly adhered in postoperative treatment, artificial dialysis therapy, and the like. Moreover, according to the present invention, there is an excellent compatibility between the acrylic polymer and acrylics oligomer, but because the acrylic oligomer is locked up in the cross-linked acrylic polymer, even though the medical tape is rolled up in a roll shape and saved under high temperature condition or saved for a long time, the leak out of acrylic oligomer is decreased, and the transfer to the substrate back can be effectively prevented. Therefore, a product that is suitable as a medical tape having significant easiness in both manufacturing and storage.

The invention claimed is:
1. A medical pressure-sensitive adhesive composition, in which an intermediate composition is cross-linked through the use of a cross-linking agent, wherein the intermediate composition contains an acrylic polymer having a cross-linkable functional group, an acrylic polymer having no cross-linkable functional group and an acrylic oligomer prepared by polymerization of monomers containing 10 to 40 percent by weight of vinyl monomer with a lactam ring, while the number average molecular weight of the acrylic polymer having a cross-linkable functional group is set at a value within the range of 300,000 to 1,500,000, the number average molecular weight of the acrylic oligomer is set at a value within the range of 1,200 to 7,000, the medical pressure-sensitive adhesive composition is made by compounding the acrylic oligomer in the range of 50 to 700 parts by weight relative to 100 parts by weight of the acrylic polymer having a cross-linkable functional group, and the additional amount of the acrylic polymer having no cross-linkable functional group is set at a value within the range of 1 to 50 percent by weight, relative to the whole amount of the medical pressure-sensitive adhesive composition.

2. The medical pressure-sensitive adhesive composition according to claim 1, wherein the acrylic oligomer contains a (meth)acrylic acid alkyl ester monomer as a monomer component, and the molar fraction of this (meth)acrylic acid alkyl ester monomer is set at a value within the range of 60 to 90 percent by mole relative to the whole amount of the oligomer.

3. The medical pressure-sensitive adhesive composition according to claim 1, wherein the acrylic oligomer includes 2-ethylhexylacrylic ester and N-vinyl-2-pyrrolidone as monomer components.

4. The medical pressure-sensitive adhesive composition according to claim 1, wherein the viscosity (25° C.) of the acrylic oligomer is set at a value within the range of 10 to 1,000 dPa·s.

5. The medical pressure-sensitive adhesive composition according to claim 1, wherein a medicament is included at content within the range of 0.1 to 30 percent by weight relative to the whole amount of medical pressure-sensitive adhesive composition.

6. A medical tape, in which a medical pressure-sensitive adhesive composition is laminated on a substrate, wherein the medical pressure-sensitive adhesive composition is prepared by cross-linking an intermediate composition containing an acrylic polymer having a cross-linkable functional group, an acrylic polymer having no cross-linkable functional group and an acrylic oligomer prepared by polymerization of monomers containing 10 to 40 percent by mole of vinyl monomer with a lactam ring through the use of a cross-linking agent, and wherein this medical tape is made by compounding the acrylic oligomer in the range of 50 to 700 parts by weight relative to 100 parts by weight of the acrylic polymer having a cross-linkable functional group, while the number average molecular weight of the acrylic polymer having a cross-linkable functional group is set at a value within the range of 300,000 to 1,500,000, and the number average molecular weight of the acrylic oligomer is set at a value within the range of 1,200 to 7,000, and the additional amount of the acrylic of the acrylic polymer having no cross-linkable functional group is set at a value within the range of 1 to 50 percent by weight, relative to the whole amount of the medical pressure-sensitive adhesive composition.

* * * * *